(12) United States Patent
Namsaraev et al.

(10) Patent No.: US 7,482,125 B2
(45) Date of Patent: Jan. 27, 2009

(54) RENATURATION, REASSOCIATION, ASSOCIATION AND HYBRIDIZATION OF NUCLEIC ACID MOLECULES

(75) Inventors: Eugeni Namsaraev, Menlo Park, CA (US); Ronald W. Davis, Palo Alto, CA (US); George Karlin-Neumann, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 96 days.

(21) Appl. No.: 11/590,281

(22) Filed: Oct. 30, 2006

(65) Prior Publication Data

US 2007/0092908 A1   Apr. 26, 2007

Related U.S. Application Data

(62) Division of application No. 09/972,031, filed on Oct. 4, 2001, now Pat. No. 7,129,044.

(60) Provisional application No. 60/239,068, filed on Oct. 4, 2000.

(51) Int. Cl.
*C12Q 1/68* (2006.01)
*C12P 19/34* (2006.01)

(52) U.S. Cl. .................. 435/6; 435/91.1; 435/91.2; 435/91.52; 435/91.53

(58) Field of Classification Search ................. None
See application file for complete search history.

(56) References Cited

U.S. PATENT DOCUMENTS

| | | | |
|---|---|---|---|
| 5,015,569 | A | 5/1991 | Pontius |
| 5,132,207 | A | 7/1992 | Kohne et al. |
| 5,474,911 | A | 12/1995 | Pontius |
| 5,747,254 | A | 5/1998 | Pontius |
| 6,013,442 | A | 1/2000 | Kolesar et al. |
| 6,027,880 | A | 2/2000 | Cronin et al. |
| 6,040,138 | A | 3/2000 | Lockhart et al. |
| 6,043,352 | A | 3/2000 | Manoharan et al. |
| 6,045,996 | A | 4/2000 | Cronin et al. |
| 6,264,825 | B1 | 7/2001 | Blackburn et al. |

OTHER PUBLICATIONS

Tenberge, et al., "Nonradioactive in situ hybridization for detection of hydrophobin mRNA in the phytopathogenic fungus Claviceps purpurea during infection of rye", European J. of Cell Biology 75: 265-272 (Mar. 1998).
Hsu, et al., "Genotyping Single-Nucleotide Polymorphisms by the Invader Assay with Dual-Color Fluorescence Polarization Detection", Clinical Chemistry 47:8 1373-1377 (2001).
Ambion Catalog Northern & Southern Analysis pp. 58-59 (2001).
Ambion Catalog Nuclease Protection Assays pp. 72-73 (2001).
Nedbal, et al., "The Association of Complementary Ribnucleic Acids can be Strongly Increased without Lowering Arrhenius Activation Energies or Significantly Altering Structures", Biochemistry 36: 13552-13557 (1997).
Brenner, et al., "In Vitro Cloning of Complex Mixtures of DNA on Microbeads: Physical Separation of Differentially Expressed cDNAs", PNAs vol. 97(4) 1665-1670 (Feb. 15, 2000).
Pontius, B., "Close encounters why unstructured, polymeric domains can increase rates of specific macromolecular association", Trends in Biochemical Sciences vol. 18: 181-186 (May 1993).
Pontius, et al., "Renaturation of Complementary DNA Strands mediated by Purified mammalian Heterogenous Nuclear Ribonucleoprotein A1 protein: Implications for a Mechanism for Rapid Molecular Assembly", Proc. Natl Acad Sci. vol. 87: 8403-8407 (Nov. 1990).
Pontius, et al., "Rapid Renaturation of Complementary DNA Strands mediated by Catonic detergents: A role for High-Probability Binding Domains in Enhancing the Kinectics of Molecular Assembly Processes", Proc. Natl Acad Sci. vol. 88: 8237-8241 (Sep. 1991).
Sambrook, J., Molecular Cloning, A Laboratory Manual, Chapter 6: Preparation and Analysis of Eukaryotic Genomic DNA, vol. 1: Information Panels 6.61-6.62.
Scheitzer, et al., "Combining Nucleic Acid Amplification and Detection", Current Opinion in Biotechnology 12: 21-27 (2001).
Shi, et al., "Enabling Large-Scale Pharmacogenetic Studies by High-Throughput Mutation Detection and Genotyping Technologies", Clinical Chemistry 47:2 164-172 (2001).
Nedbal, et al., "Mechanistic insights into p53-promoted RNA-RNA annealing", J. Mol. Biol. (1997) 266, 677-687.
Nedbal, et al., "Facilitators of RNA-RNA annealing: implications for the catalytic cycle of hammerhead ribozymes", Biochemical society transactions, vol. 24, No. 3., (1996), pp. 615-618.
Kim et al. Antisense Research and Development 5:49 (1995).

*Primary Examiner*—James Martinell
(74) *Attorney, Agent, or Firm*—Carol L. Francis; Bozicevic, Field & Francis LLP

(57) ABSTRACT

The present invention features methods and compositions for the renaturation, hybridization, association, or reassociation of nucleic acids that combines both acceleration of the reaction rate and improved specificity.

26 Claims, No Drawings

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: pm60L20

<400> SEQUENCE: 1
agcatcacca gaagaaacag                                              20

<210> SEQ ID NO 2
<211> LENGTH: 20
<212> TYPE: RNA
<213> ORGANISM: Artificial Sequence
<220> FEATURE:
<223> OTHER INFORMATION: Tch2.1L20

<400> SEQUENCE: 2
cuguuucuuc uggugaugcu                                              20

<210> SEQ ID NO 3
<211> LENGTH: 25
```

```
<212> TYPE: RNA
<213> ORGANISM: Artificial Sequence
<220> FEATURE:
<223> OTHER INFORMATION: Tch2.1L25

<400> SEQUENCE: 3
cguuacuguu ucuucggug augcu                                              25

<210> SEQ ID NO 4
<211> LENGTH: 20
<212> TYPE: DNA
<213> ORGANISM: Artificial Sequence
<220> FEATURE:
<223> OTHER INFORMATION: c60L20

<400> SEQUENCE: 4
ctgtttcttc tggtgatgct                                                   20

<210> SEQ ID NO 5
<211> LENGTH: 279
<212> TYPE: RNA
<213> ORGANISM: Artificial Sequence
<220> FEATURE:
<223> OTHER INFORMATION: Tch2

<400> SEQUENCE: 5
gaauucgucc agaucuauga auccguuacc gucuagaucg aauuguuuca ucaucguuac        60
uguuucuucu ggugaugcug uuggugagag agcgcggauc acuucuuuga gcucgucgac       120
ggagauuuuc ccgucgccgu uuuugucgaa ucguggaag acuuuuuga ugucguccau         180 ugauccuaaa cagcuacgaa caacuccguu cuucgaugac auuguugaag aaauugagau       240
uuugagauuu gagauuugag agaagaaaaa accgaauuc                              279

<210> SEQ ID NO 6
<211> LENGTH: 20
<212> TYPE: DNA
<213> ORGANISM: Artificial Sequence
<220> FEATURE:
<223> OTHER INFORMATION: pm203.L20

<400> SEQUENCE: 6
atgtcatcga agaacggagt                                                   20

<210> SEQ ID NO 7
<211> LENGTH: 60
<212> TYPE: DNA
<213> ORGANISM: Artificial Sequence
<220> FEATURE:
<223> OTHER INFORMATION: pm60L2060

<400> SEQUENCE: 7
gaaatcgtca aaatcgctta cagttcaggt ctccagtcat agcatcacaa gaagaaacag       60

<210> SEQ ID NO 8
<211> LENGTH: 20
<212> TYPE: DNA
<213> ORGANISM: Artificial Sequence
<220> FEATURE:
<223> OTHER INFORMATION: B4pm1

<400> SEQUENCE: 8
tggtatgtgc tttctcgtgt                                                   20

<210> SEQ ID NO 9
```

```
<211> LENGTH: 20
<212> TYPE: DNA
<213> ORGANISM: Artificial Sequence
<220> FEATURE:
<223> OTHER INFORMATION: B4pm2

<400> SEQUENCE: 9
tttagcgggg tgatgcctgt                                              20
```

RENATURATION, REASSOCIATION, ASSOCIATION AND HYBRIDIZATION OF NUCLEIC ACID MOLECULES

CROSS REFERENCE TO RELATED APPLICATIONS

The present application is a divisional application of Ser. No. 09/972,031, filed Oct. 4, 2001, now issued as U.S. Pat. No. 7,129,044 on Oct. 31, 2006, which application claims priority under 35 U.S.C. § 119(e) to U.S. provisional application No. 60/239,068, filed Oct. 4, 2000, the disclosure of which is incorporated herein by reference in its entirety.

STATEMENT REGARDING FEDERALLY SPONSORED RESEARCH

Aspects of the present invention may have been made under NIH Grant HG00205; the government may have certain rights in this invention.

FIELD OF THE INVENTION

The present invention relates to methods and compositions for the highly specific renaturation, association, reassociation or hybridization of single-stranded nucleic acid pairs.

BACKGROUND OF THE INVENTION

The association, reassociation, renaturation or hybridization of complementary nucleic acids (RNA or DNA) in vitro has proven to be a powerful tool for analyzing the genetic material. While nucleic acid reassociation has been used to answer many important questions, two major limitations for its use in many significant biological experiments are the rate and specificity of the association.

Association, reassociation, renaturation, and hybridization are generally used interchangeably to refer to the formation of double-stranded nucleic acids from two single-stranded nucleic acid molecules, whose nucleotide composition allows enough hydrogen-bonds to form between corresponding nucleotides (C-G and A-T or A-U) of these paired single-stranded molecules to prevent the double-stranded molecules from denaturation. The formation of a duplex molecule with all perfectly formed hydrogen-bonds between corresponding nucleotides will be referred as "matched" and duplexes with single or several pairs of nucleotides that do not correspond as "mismatched." Any combination of single-stranded RNA or DNA molecules can form duplex molecules (DNA:DNA. DNA:RNA, RNA:DNA. or RNA:RNA) under appropriate experimental conditions.

The thermodynamic parameters of association for completely matched nucleic acids are well understood and depend on the nucleotide composition of each pair, their concentration, and the composition of the solution used for these reactions. The nucleotide composition of single-stranded molecules directly influences the temperature of the reaction. Generally, longer molecules, RNA:RNA duplexes, and molecules containing higher G and C nucleotide composition have a higher melting temperature (Tm, the temperature at which 50% of the double-stranded molecules are denatured). In order to achieve the maximum rate, the reactions are usually performed 10-20 degrees Centigrade below the Tm.

Because the kinetics of these reactions are second-order, the rate of the reaction is determined by the concentration of the most abundant species. Low concentrations of the hybridizing species lengthens the time of the reaction. Therefore, the reaction time is one concern when reassociating nucleic acids. It is common to perform the reaction for several hours or even days; however shorter incubation times can be achieved by increasing the quantities of single-stranded nucleic acid molecules, though this is often not desirable.

Finally, the reaction rates depend on the ionic strength of the solution. The single-stranded nucleic acid molecules are negatively charged and thus repel one another; therefore salt should be included for efficient hybridization. The rate varies significantly with decreasing ionic strength below 0.4 M, but is less dependent at higher salt concentrations.

From a theoretical viewpoint, the association of two completely matched single-stranded molecules is well understood. However, in practice, populations of molecules interact resulting in a more complex situation, especially in mixtures of many different single-stranded molecules. A major difficulty in the association of complex mixtures of nucleic acids is the tendency to form duplexes containing one or several mismatched (mispaired, nonspecific) nucleotides in addition to the completely matched duplexes. The degree of discrimination between perfectly matched duplexes and mismatched duplexes is referred to as "specificity." Generally, duplexes with mismatched nucleotides have a lower Tm than matched ones; however, the magnitude of the decrease depends on many factors such as the duplex length, the position of the mismatched nucleotide pair in the duplex, the type of mismatch (G-A, G-G, G-T, C-C, and etc.), and the neighboring nucleotide composition around the mismatch. To maintain specificity in duplex molecule formation, the association reactions are carried out at temperatures as close as possible to the Tm to prevent formation of mismatched duplexes. Denaturation curves of duplex nucleic acids have a sigmoidal form, and duplexes with different nucleotide sequences but similar Tm's are generally present in the mixture, at least to some extent, at any incubation temperature.

From a practical point of view, shorter single-stranded nucleic acid molecules which have lower Tm's are preferred for a more specific association reaction. With these shorter molecules, even a single nucleotide mismatch can significantly affect the stability of the duplex resulting in a significant decrease in its Tm, though for longer molecules it often does not have such a marked effect. The destabilizing effect of the mismatch is most accentuated at the Tm of the perfectly matched duplex, thus allowing the best discrimination between them to occur at this temperature. There are several different methods for calculating the Tm for short single-stranded nucleic acids (oligos). A generally accepted, common formula is:

$$Tm(°C.) = (\text{number of C's and G's}) \times 4 + (\text{number of A's and T's}) \times 2.$$

Thus, for example, for a 20-nucleotide long oligo with equal contents of A, T. G. and C, the Tm of the perfectly matched duplex with a second complementary oligo will be around 60° C.; the difference between this and the single nucleotide mismatched duplex can be as little as 2° C. In such a case, incubation at the Tm will form 50% matched duplex oligos and a considerable fraction of mismatched duplexes. However incubation at temperatures 10-20° C., below the Tm, where the rate is highest, will form both duplexes with high efficiency (95%), making it impossible to distinguish the different species by Tm alone.

Moreover, the Tm for each mismatched duplex is difficult to calculate and can be determined only experimentally. The specificity can be increased by decreasing salt concentration, and the association can be performed even in the absence of salt. But, again, the optimum conditions for specific association can only be determined experimentally for each pair of single-stranded nucleic acids. Moreover, low salt concentration greatly decreases the rate of the reaction.

All of the problems described above make it difficult to achieve both rapid reaction rate and high specificity in association of complex nucleic acid mixtures. And although a number of techniques have been developed that increase the basic reaction rate by a factor of up to 1,000 times, an increase in the rate of the reaction does not necessarily—and normally does not—provide an acceptable level of specificity relative to the basic reference reaction in the single phase system.

The most common technique for accelerating the reaction rate has been to increase the salt concentration up to 10 M (see, e.g., U.S. Pat. No. 5,132,207). The addition of various salts to the hybridization solution can increase the rate of the reaction thousands of times. The effect of acceleration using increased salt concentration is achieved by aggregation or precipitation of nucleic acids, thereby increasing local nucleic acid concentrations. Because the specificity of association is decreased with increasing salt concentration, this method of accelerating association is likely not useful in precise mismatch discrimination; no data has been presented to date that suggests otherwise.

Another approach to accelerating the rate of nucleic acid association is the two-phase phenol aqueous emulsion technique (see, e.g., U.S. Pat. No. 5,132,207). However, it can only be used effectively for acceleration of DNA:DNA duplex molecules; the method is not effective for formation of DNA:RNA or RNA:RNA molecules. The phenol aqueous emulsion technique can accelerate DNA:DNA duplex association greater than about 1000-fold; however, RNA:RNA and RNA:DNA duplex formation is accelerated less than about 100 fold. This technique is very sensitive to phenol concentration and temperature. Moreover, the maximum rate of the reaction is reached at higher salt concentrations. The acceleration again is achieved by "increasing the DNA concentration at the phenol:aqueous interface", and again a high concentration of salt should decrease discrimination between match and mismatch formation. No experiments were reported that would have determined the specificity of association in this method.

Other prior methods focus only on acceleration of association, but not under conditions that would provide for specificity for detection of, for example, only a few nucleotide differences (e.g., single nucleotide changes). In addition, most work has focused on formation of DNA:DNA or RNA:RNA duplexes; little progress on the acceleration of DNA:RNA or RNA:DNA duplexes has been reported.

For example, Pontius has reported that heterogeneous nuclear ribonucleoprotein A can accelerate the association rate of DNA:DNA duplexes (Pontius et al. (1990) *Proc. Natl. Acad. Sci. USA* 87:8403-8407; U.S. Pat. No. 5,747,254) and that cationic detergents like cetyltrimethylammonium bromide (CTAB) can also accelerate the association rate of DNA:DNA duplexes (U.S. Pat. No. 5,474,911; Pontius et al. (1991) *Proc. Natl. Acad. Sci. USA* 88:8237-8241), likely by a similar mechanism. In addition, Pontius reports that even 1 mM CTAB is strongly stabilizing for DNA:DNA helices, even at temperatures well above the melting temperature expected for the double-stranded DNA in the absence of detergent (Pontius et al (1991) *Proc. Natl. Acad. Sci. USA* 88:8237-8241). See also, Sambrook et al., *Molecular Cloning: A Laboratory Manual* (3$^{rd}$ ed.), Cold Spring Harbor Laboratory Press, 2001 (ISBN:0-87969-576-5), at 6.62: "Rapid Hybridization Buffers."

Publications by other researchers have shown that CTAB and other CTAB-like detergents can accelerate formation of RNA:RNA molecules (Nedbal et al., *Biochemistry* (1997) 36:13552-13557). However, none of these references addressed the specificity issue, and none examined the association of DNA:RNA or RNA:DNA. In short, although CTAB was demonstrated to have accelerating effects upon association of DNA:DNA and RNA:RNA duplexes, there was no demonstration of acceleration of the association of DNA:RNA or RNA:DNA duplexes, nor was there any evidence regarding the specificity of association of any nucleic acid duplexes.

A number of hybridization accelerants of unknown composition are available commercially (such as ULTRAHYB™ and HYBSPEE™, Ambion, Austin, Tex., USA); none are described as increasing simultaneously the rate of association and specificity of association.

Discovery of methods and compositions to accelerate association of RNA:DNA molecules in a manner that provides for high specificity (e.g., no mismatched sequences are reassociated, thus allowing for detection of, for example, single nucleotide differences between two sequences) would greatly advance the molecular genomics field.

SUMMARY OF THE INVENTION

The present invention addresses these and other needs in the art by providing methods, compositions and kits for the renaturation, hybridization, association, or reassociation of nucleic acids that combine both acceleration of the reaction rate and improved specificity.

A primary object of the invention is to provide methods for the renaturation, hybridization, association, or reassociation of nucleic acids that combines both features, acceleration of the reaction rate and improved specificity, particularly in aqueous solutions.

Another object of the present invention is to provide methods whereby accelerated association with high specificity can be performed in complex nucleic acid mixtures, without incubation at elevated temperatures, and which are widely applicable to a variety of hybridization aims.

Still another object of the invention is to provide a method for fast and easy removal of detergent from the incubation solution used during association, so that the duplexes formed according to the methods of the invention can be readily used in subsequent enzymatic steps.

An advantage of the invention is that the methods provide for accelerated association of single-stranded nucleic acid molecules in a manner that also provides for extreme specificity, e.g., the method provides for rapid detection of single nucleotide differences between two nucleic acid sequences (e.g., between an RNA sequence and a DNA sequence).

Another advantage of the invention is that the methods do not require the use of high concentrations of salt (e.g., on the order of several molar concentrations, e.g., 10 M salt) during duplex formation. High concentrations of salt can interfere with the activity of enzymes used in subsequent manipulation of the associated duplexes.

These and other objects, advantages, and features of the invention will become apparent to those persons skilled in the art upon reading the details of the invention as more fully described below.

DETAILED DESCRIPTION OF THE INVENTION

The present invention is based on two surprising discoveries: first, that certain agents that accelerate the rate at which complementary single-stranded nucleic acid molecules form base-paired double-stranded duplex molecules ("association enhancers", exemplified herein by cationic detergents such as cetyltrimethylammonium bromide, "CTAB", and related surfactants) can also greatly increase the specificity or selectivity of formation of completely matched duplexes over mismatched ones; and second, that this increase in selectivity is observed, at least under the tested conditions, for RNA:DNA and DNA:RNA duplexes, but not for formation of DNA:DNA duplexes. The concomitant increase in both the rate and the specificity of hybridization (for other than DNA:DNA duplexes) makes possible improved methods for discriminating between nucleic acid targets and improved methods for performing hybridization-primed enzymatic reactions. We have also observed that the specific association enhancer reduces both the GC content sensitivity and temperature sensitivity of the specific hybridization of RNA to DNA, which permits a wider range of probes and/or targets to be used under a common set of hybridization conditions than has hitherto been possible.

Before the present invention is described in further detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

In a nucleic acid hybridization reaction in which two single-stranded nucleic acid molecules bind to one another through conventional base pairing to form a duplex, either of the two strands of the duplex can be denominated the "probe" with the other, complementary, strand of the duplex termed the "target". Accordingly, the designation herein of "probe" and "target" with respect to the strands of a duplex is not to be construed as limiting, inasmuch as the strand denominated as the "probe" can equally be termed the "target". Analogously, the terms "first strand" and "second strand" of a duplex are not meant herein to be limiting with respect to the sense of the strand, and either can refer to the sense or antisense strand of the duplex (e.g., the first strand may be the sense strand and the second strand may be the antisense strand, or vice versa). Similarly, when a duplex is denoted as RNA:DNA or DNA:RNA, the order will not necessarily indicate which of the two molecules encodes the sense strand.

The term "specific association" means association of two single-stranded nucleic acid molecules with high specificity (e.g., a level of specificity that allows for discrimination between matched and mismatched duplexes at the level of a single nucleotide difference).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these ranges may independently be included in the smaller ranges also encompassed within the invention, subject to any specifically excluded limit in the stated range. Where the stated range includes one or both of the limits, ranges excluding either or both of those included limits are also included in the invention.

It must be noted that as used herein and in the appended claims, the singular forms "a", "an", and "the" include plural referents unless the context clearly dictates otherwise. Thus, for example, reference to "a nucleic acid duplex" includes a plurality of such nucleic acid duplexes and reference to "the association enhancer" includes reference to one or more association enhancers and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

As noted above, we have discovered that certain association enhancers, herein termed "specific association enhancers", act in certain hybridization reactions both to increase the reaction rate and improve the specificity of the hybridization.

The specific association enhancers useful in the present invention are selected from compounds that can bind noncovalently and in a sequence-independent manner to single-stranded nucleic acids and that, when so bound, present at least one weakly interacting, relatively unstructured, polymeric domain for subsequent intermolecular interactions. Without intending to be bound by theory, these agents are believed to enhance the rate of nucleic acid association by mediating non-specific, and thus high probability, transient binding interactions between nucleic acid strands, facilitating subsequent sequence-specific bond formation.

Such agents include, inter alia, certain naturally occurring proteins, such as heterogeneous nuclear ribonucleoprotein (hnRNP) A1, and certain chemical compounds.

One particular class of association enhancers from which specific association enhancers suitable for use in the present invention can be selected, at present preferred, are cationic detergents. "Cationic detergent" refers to a detergent having both (1) a positive charge and (2) at least one hydrophobic side-chain. Without intending to be bound by theory, it is believed that the detergent's positive charge mediates binding of the detergent to phosphates of the nucleic acid phosphodiester backbone, while the hydrophobic side chains of the detergent molecules mediate nonspecific, transient, associations between nucleic acid molecules.

Cationic detergents are well known in the art, and are described, inter alia, in standard texts such as *McCutcheon's 2001 Volume 1: Emulsifiers & Detergents*, Allured (ed.), McCutcheon Div Mc Pub Co (ISBN: 0944254780), the North American and International Editions of which cover over 10,000 emulsifier and detergent products worldwide; and *Handbook of Detergents: Properties* (Surfactant Science, 82), Zoller et al. (Eds.), Marcel Dekker (ISBN: 0824714172), 1999.

Cationic detergents from which specific association enhancers suitable for use in the present invention can be selected, include those given by the following formula:

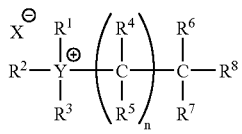

wherein n≧12, wherein R1, R2, R3, R4, R5, R6, R7, and R8 are each independently hydrogen or an alkyl group interrupted by and/or having appending combinations of alkyls, aromatics, carbonyls (including acids, aldehydes, amides, esters and ketones), cyclics, haloalkyls, heteroatoms and unsaturations, wherein $X^-$ is bromide, chloride, iodide, acetates, alkoxides, borates, carbonates, carboxylates (including oxalates, succinates, tartrates), sulfates, sulfites, sulfonates, phosphates, nitrates, nitrites, hydroxide or other transitional or non-transitional metals, and wherein $Y^+$ is nitrogen, phosphorus, or sulfur.

Among such cationic detergents are usefully tetraalkylammonium salts, e.g., those having a positive charge from an ammonium ion and an alkyl chain providing a hydrophobic tail. It will be readily apparent to the ordinarily skilled artisan upon reading the present specification that the present invention is not limited to the specific exemplary association enhancers and specific association enhancers described herein, and that variations upon the chemical structure of, for example, the exemplary cationic detergents can be made and still provide the desired advantageous properties of the specific association enhancers.

In an embodiment that is at present preferred, the association enhancer is a cationic detergent, particularly a cetyltrimethylammonium salt, particularly cetyltrimethylammonium bromide (CTAB), cetyltrimethylammonium chloride (CTAC), cetyltrimethylammonium hydrosulfate (CTAS), and cetyltrimethylammonium with other counter-ions.

In another embodiment, the association enhancer is a modified CTAB (or CTAB-like) detergent.

"Modified CTAB detergent" or "CTAB-like detergent" as used herein refers to a detergent that is modified relative to CTAB by virtue of N-substitutions, variations in chain length, phosphorium or sulforium substitutions for the nitrogen atom, and other modifications readily apparent to the skilled artisan which alter the chemical structure of the detergent, but retain activity as an association enhancer. Thus, in one embodiment, the association enhancer is a modified CTAB having one or more N-methyl group substituted with ethyl, butyl, and other higher alkyl groups. Further, the nitrogen atom in the CTAB head-group may be substituted by phosphate or sulphate.

In yet another embodiment, the association enhancer is a modified CTAB or CTAB-like detergent having variations in the length of the alkyl chain. In general, the alkyl chain is at least about 13 carbons, with more than 12 carbons being preferred. The long alkyl chain can be saturated or unsaturated, or can contain side groups. Particular embodiments include tetradecyltrimethylammonium bromide (TTAB), and octadecyltrimethylammonium bromide (OTAB).

Given the large number of compounds embraced by the definition of association enhancer set forth above, the following simple routine test can be used to test any potential such agent for suitability as a specific association enhancer in the methods and compositions of the present invention.

In order to determine whether a potential agent is a specific association enhancer suitable for use in the present invention the following four hybridization reactions are performed in parallel. All reactions are performed in solution containing 10 mM Tris-HCl (pH 8.0), 1 mM EDTA. 50 mM NaCl. Sequences are as follows:

```
pm60L20 (DNA):
5'-AGCATCACCAGAAGAAACAG-3'          [SEQ ID NO: 1]

Tch2.1L20 (RNA):
5'-CUGUUUCUUCUGGUGAUGCU-3'          [SEQ ID NO: 2]

Tch2.1L25 (RNA):
5'-CGUUACUGUUUCUUCUGGUGAUGCU-3'     [SEQ ID NO: 3]
```

First, two standard hybridizations without addition of the agent:
a) 1 nM $^{32}$P 5'-labeled pm60L20 DNA oligonucleotide and 200 nM complementary Tch2.1L20 RNA oligonucleotide
b) same as a) but the pm60L20 DNA oligonucleotide has a single nucleotide change of C to A at the $8^{th}$ position from the 5' end Second, hybridizations with addition of the potential agent to 1 mM:
c) 1 nM $^{32}$P 5'-labeled pm60L20 DNA oligonucleotide and 1 nM complementary Tch2.1L20 RNA oligonucleotide
d) same as c) but the pm60L20 oligonucleotide has a single nucleotide change of C to A at the $8^{th}$ position from the 5' end The mixtures are heated first to 85° C., and then incubated at 42° C. respectively for 40 min (reactions (a) and (b)), and 5 min (reactions (c) and (d)). Aliquots are then assayed for formation of double stranded molecules by temperature-controlled (20° C.), 15% PAGE, followed by autoradiography. The formation of double-stranded molecules is determined for all four reactions. (If Tch2.1L25 is substituted in the reactions for Tch2.1L20, the formation of duplexes can be also assayed by single nucleotide extension analysis by 15% denaturing PAGE, followed by autoradiography.)

The ratio of mismatch:match duplex formation is separately calculated for reactions (b) and (a) (no agent), and (d) and (c) (with agent), respectively. If the ratio with the agent present is smaller than the ratio in the absence of the agent, indicating decreased formation of mismatched double-stranded molecule in the presence of the agent, the agent is a specific association enhancer suitable for use in the present invention.

Although specific association enhancers that increase the reaction rate to any degree are useful in the practice of the present invention, it is preferred that the specific association enhancer greatly increase the reaction rate.

In the foregoing context, "greatly increase the reaction rate" means a rate increase of at least 50 times over the regular non-accelerated hybridization rate (e.g., without an effective amount of an association enhancer (e.g., CTAB or CTAB-like detergent)). In general, the rate of association increases at least about 100 times, generally at least about 300 times, up to 500 times to 1,000 or several thousand times or more over the non-accelerated reaction.

Accelerated association of nucleic acid molecules is generally described in terms of an association rate constant. "Association rate constant" in the context of nucleic acid refers to the rate at which complementary members of a binding pair form a complex, e.g., the rate at which two nucleic acid molecules are associated. The association rate constant is generally measured in liters of complex formation per mole per second. For the case where two molecules are coming together to form a complex, (e.g., A+B⇌AB), the rate of formation is equal to $k_a[A][B]$, where [A] is the concentration of A in solution, [B] is the concentration of B in solution, and $k_a$ is the association rate constant. Lower rates of association exist where there is little mutual attraction over significant distances and where complex formation averages multiple random collisions between members before complex formation occurs. Binding members having low $k_a$ rely on Van der Waal forces or hydrogen bond formation to provide the energy of complex formation. High rates of association exist where the two molecules mutually attract each other to bring about a greater number of contacts which increase the opportunity for complex formation. Such molecules rely on electrostatic and hydrophobic interactions.

The association rate constant can vary depending on a variety of factors such as, for example, the types of interactions involved and the concentration of the nucleic acid molecules. Under conditions where little strand melting occurs (e.g., below the Tm of the nucleic acid) the rate of association can be calculated by measuring the amount of loss of single-stranded substrate at various times, or by measuring the amount of formation of double-stranded product. The amount of single strands can be measured by S1 nuclease sensitivity assays. The amount of double-stranded material can be measured by hydroxyapatite binding. Optical hyperchromicity can also be used. Alternatively, single strands can be separated from double strands by gel electrophoresis by virtue of their different mobilities. For DNA molecules with defined ends, the association rate constant for annealing can be derived from the equation:

$$H=(1+k_a C_o t)^{-1}$$

where H=fraction of single strands remaining; $k_a$=association rate constant; $C_o$=original concentration of nucleotides; and t=time of incubation in seconds. (*Nucleic Acid Hybridization* Ed. Hames, Higgins IRL Press (1985)).

And although specific association enhancers that improve the specificity of hybridization to any degree are useful in the practice of the present invention, it is preferred that the specific association enhancer significantly improve the specificity of the hybridization reaction.

As used herein, significantly improved specificity means a decrease in the mismatch:match ratio in the presence of the specific association enhancer in either of the above-described tests of at least about 1.2 fold, 1.3 fold, 1.4 fold, 1.5 fold, 2 fold, to 3 fold, 4 fold, 5 fold, 6 fold, 7 fold, 8 fold, 9 fold, to 10 fold, and often at least up to about 50 fold, and can be at least about 100 fold or more. Where the duplex has two or more mismatches, specificity is improved using the method of the invention even more drastically. For example, with two mismatches in the duplex, specificity is improved using the method of the invention at least about 50 times, 60 times, 70 times, and at times up to 100 times relative to specificity in the absence of an association enhancer. In general, when used with duplexes of about 20 nucleotides in length (or having 20 nucleotides of sequence complementarity) and having a single nucleotide mismatch, we have observed that the methods of the invention provide for a several-fold increase in specificity for most positions of a mismatch within the region of complementary sequence.

In a first aspect, the invention takes advantage of the increase in rate and specificity of hybridization effected by inclusion of a specific association enhancer to provide a method of discriminating between nucleic acid targets. The method comprises identifying differences in the extent of nucleic acid duplex formation between each of the nucleic acid targets and a common nucleic acid probe, wherein the duplexes are formed in the presence of an effective amount of a specific association enhancer under conditions suitable for association of duplexes.

As mentioned above, and demonstrated in the Examples below, we have not observed the specific association enhancers to improve specificity of DNA:DNA duplex formation under the tested conditions. Thus, in embodiments of the method having particular interest, duplexes are formed between DNA and RNA (DNA:RNA), DNA:modified DNA ("mDNA"), RNA:RNA, or RNA:mDNA, where either of probe or target can have the first-mentioned of the two compositions. By modified DNA (mDNA) is intended a molecule that displays RNA-like features. Modified DNA molecules that display RNA-like features include, e.g., nucleic acids that are chimeric, i.e., that include both ribonucleotides and deoxyribonucleotides in phosphodiester linkage, or that have nucleotides modified at the 2' carbon of ribose (e.g., 2-methoxy-modified DNA, 2'-O-alkyl DNA).

Typically, the region of complementarity between the common probe and one or more of the targets is at least about 15 nt in length, often at least about 16 nt, 17 nt, 18 nt, 19 nt, 20 nt, 21 nt, 22 nt, 23 nt, 24 nt, or even 25 nt, 26 nt, 27 nt, 28 nt, 29 nt, or 30 nt in length, although shorter is permissible. "Region of complementarity" refers to a region over which the sequences of probe and target share, or are suspected to share, complementary sequences, e.g., a region over which the sequences would form a matched duplex. Also typically, the region of complementarity is no more than about 30 nt in length, often no more than about 29 nt, 28 nt, 27 nt, 26 nt, 25 nt, 24 nt, 23 nt, 22 nt, 21 nt, 20 nt, 19 nt, 18 nt, 17 nt, 16 nt, or even no more that 15 nt in length, although longer is permissible. Frequently, the probe (or target) is between about 16 and 30 nucleotides long, with a length of about 20 nucleotides being preferred under currently tested conditions.

The region of complementarity can be present within nucleic acids that have sequence additional thereto. In such embodiments, the additional portion of the single-stranded molecule can be of any length, with the region of complementarity positioned anywhere within the larger molecule. Indeed, the complete molecule containing the region of complementarity can be substantially longer, e.g., the nucleic acid can be 1000 nt to 100,000 nt or longer, and may encompass an entire chromosome.

Conversely, the probe (and/or target) can at times be only as long as the region of complementarity. In such embodiments, the probe (and/or target) is typically at least about 15 nt in length, often at least about 16 nt, 17 nt, 18 nt, 19 nt, 20 nt, 21 nt, 22 nt, 23 nt, 24 nt, or even 25 nt, 26 nt, 27 nt, 28 nt, 29 nt, or 30 nt in length, although shorter is permissible. Also typically, the aforesaid single stranded molecule is no more than about 30 nt in length, often no more than about 29 nt, 28 nt, 27 nt, 26 nt, 25 nt, 24 nt, 23 nt, 22 nt, 21 nt, 20 nt, 19 nt, 18 nt, 17 nt, 16 nt, or even no more than 15 nt in length, although longer is permissible. Frequently, the probe (or target) is between about 16 and 30 nucleotides long, with a length of about 20 nucleotides being preferred under currently tested conditions.

Useful targets (equally, useful probes) include, e.g., genomic DNA, heteronuclear RNA. mRNA, or cDNA derived from one or more cells of prokaryotic origin or eukaryotic origin, or nucleic acids derived from one or more virions, drawn from one or from a plurality of individuals. Also useful as probes (targets) are synthetic, that is, chemically-synthesized, typically by solid-phase chemical synthesis, oligonucleotides (typically DNA, although permissibly RNA or mDNA), the sequence of which is predicated, at least in part, on genomic sequence or sequence derived from expressed transcripts.

Cells from which target (probe) nucleic acids can usefully be drawn include mammalian cells, particularly human cells, cells from related primates, such as chimpanzee, monkeys (including rhesus macaque), baboon, orangutan, and gorilla, and cells from rodents typically used as laboratory models, such as rats, mice, hamsters and guinea pigs. Target nucleic acids can also usefully be derived from cells from lagomorphs, such as rabbits; and from larger mammals. such as livestock, including horses, cattle, sheep, pigs, goats, and bison. Also useful are cells from fowl such as chickens, geese, ducks, turkeys, pheasant, ostrich and pigeon; fish such as zebrafish, salmon, tilapia, catfish, trout and bass; and domestic pet species, such as dogs and cats.

Plant cells from which target (probe) nucleic acids can usefully be derived include, for example, experimental model plants, such as *Chlamydomonas reinhardtii*, *Physcomitrella patens*, and *Arabidopsis thaliana*; crop plants such as cauliflower (*Brassica oleracea*), artichoke (*Cynara scolymus*); fruits such as apples (*Malus*, e.g. *Malus domesticus*), mangoes (*Mangifera*, e.g. *Mangifera indica*), banana (*Musa*, e.g. *Musa acuminata*), berries (such as currant, *Ribes*, e.g. *rubrum*), kiwifruit (*Actinidia*, e.g. *chinensis*), grapes (*Vitis*, e.g. *vinifera*), bell peppers (*Capsicum*, e.g. *Capsicum annuum*), cherries (such as the sweet cherry, *Prunus*, e.g. *avium*), cucumber (*Cucunus*, e.g. *sativus*), melons (*Cucumis*, e.g. *melo*), nuts (such as walnut, *Juglans*, e.g. *regia*; peanut, *Arachis hypogeae*), orange (*Citrus*, e.g. *maxima*), peach (*Prunus*, e.g. *Prunus persica*), pear (*Pyra*, e.g. *communis*), plum (*Prunus*, e.g. *domestica*), strawberry (*Fragaria*, e.g. *moschata* or *vesca*), tomato (*Lycopersicon*, e.g. *esculentum*); leaves and forage, such as alfalfa (*Medicago*, e.g. *sativa* or *truncatula*), cabbage (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*); seeds, including oilseeds, such as beans (*Phaseolus*, e.g. *vulgaris*), pea (*Pisum*, e.g. *sativum*), soybean (*Glycine*, e.g. *max*), cowpea (*Vigna unguiculata*), mothbean (*Vigna aconitifolia*), wheat (*Triticum*, e.g. *aestivum*), sorghum (*Sorghum* e.g. *bicolor*), barley (*Hordeum*, e.g. *vulgare*), corn (*Zea*, e.g. *mays*), rice (*Oryza*, e.g. *sativa*), rapeseed (*Brassica napus*), millet (*Panicum* sp.), sunflower (*Helianthus annuus*), oats (*Avena sativa*), chickpea (*Cicer*, e.g. *arietinum*); tubers, such as kohlrabi (*Brassica*, e.g. *oleraceae*), potato (*Solanum*, e.g. *tuberosum*) and the like; fiber and wood plants, such as flax (*Linum*, e.g. *Linum usitatissimum*), cotton (*Gossypium* e.g. *hirsutum*), pine (*Pinus* spp.), oak (*Quercus* sp.), eucalyptus (*Eucalyptus* sp.), and the like; and ornamental plants such as turfgrass (*Lolium*, e.g. *rigidum*), petunia (*Petunia*, e.g x *hybrida*), hyacinth (*Hyacinthus orientalis*), carnation (*Dianthus* e.g. *caryophyllus*), delphinium (*Delphinium*, e.g. *ajacis*), Job's tears (*Coix lacryma-jobi*), snapdragon (*Antirrhinum majus*), poppy (*Papaver*, e.g *nudicaule*), lilac (*Syringa* e.g. *vulgaris*), hydrangea (*Hydrangea* e.g. *macrophylla*), roses (including *Gallicas, Albas, Damasks, Damask Perpetuals, Centifolias, Chinas*, Teas and Hybrid Teas), orchids, and ornamental goldenrods (e.g *Solidago* spp.).

Given the conservation of basic metabolic pathways among all eukaryotes, target (probe) nucleic acids can also usefully be derived from lower eukaryotes, such as yeasts, particularly *Saccharomyces cerevisiae*, *Schizosaccharomyces pombe*, *Pichia* species, such as *methanolica*, *Ustillago maydis*, and *Candida* species, or from multicellular eukaryotes such as *C. elegans*, zebra fish, and *Drosophila melanogaster*.

Where the target (equally, probe) is double-stranded, such as genomic DNA or double-stranded PCR amplicons thereof, the double-stranded duplex is rendered single-stranded before hybridization. In addition, or in the alternative, the target (equally, probe) can be fragmented before hybridization.

Because the specific association enhancers appear to decrease the GC content sensitivity and temperature sensitivity of duplex formation, the number of targets that can be discriminated in the method of the present invention can be as few as two, but also can include 3, 4, 5, 6, 7, 8, 9, 10, 20, 30, 50, 100, 500, 1000, 10,000, 20,000, 30,000, 40,000, or 50,000 or more. Indeed, the methods of the present invention find particular utility in highly multiplexed analyses performed in a single hybridization reaction. The plurality of targets can be discrete molecules. Alternatively or in addition, the targets to be discriminated can be separate portions of a contiguous sequence, such as an entire chromosome. The plurality of targets to be discriminated can be present together with at least one common probe in a single common hybridization reaction or, as in the test set forth above for identifying suitable specific association enhancers, in separate reactions.

Furthermore, inasmuch as a plurality of probes can also be used, the total number of duplexes that can be discriminated in the method of the present invention can be as few as two, but also can include 3, 4, 5, 6, 7, 8, 9, 10, 20, 30, 50, 100, 500, 1000, 10,000, 20,000, 30,000, 40,000, or 50,000 or more. Indeed, the methods of the present invention find particular utility in highly multiplexed analyses performed in a single hybridization reaction.

The hybridization reactions can be performed with each of probe and target in solution. Such solution hybridizations are single phase reactions; that is, do not separate into aqueous and organic phases.

Alternatively, either probe or target can be immobilized on a substrate. The substrate can be solid or porous, planar or non-planar, unitary or distributed. The probe (or target) can be immobilized alone on the substrate, or, in an alternative embodiment further described below, can be immobilized on a substrate with a plurality of other probes or targets, thus providing an array.

For example, the nucleic acids of the present invention can usefully be bound to a porous substrate, commonly a membrane, typically comprising nitrocellulose, nylon, or positively-charged derivatized nylon. Alternatively, the probe or target nucleic acids can also usefully be bound to a solid substrate, such as glass, although other solid materials, such as amorphous silicon, crystalline silicon, or plastics, can also be used. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, cellulose acetate, cellulose nitrate, nitrocellulose, or mixtures thereof. Typically, the solid substrate will be rectangular, although other shapes, particularly disks and even spheres (e.g., microspheres), present certain advantages.

The nucleic acids of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays.

As used herein, the term "microarray" and the equivalent phrase "nucleic acid microarray" refer to a substrate-bound collection of plural nucleic acids, hybridization to each of the plurality of bound nucleic acids being separately detectable. The substrate can be solid or porous, planar or non-planar, unitary or distributed.

As so defined, the term "microarray" and phrase "nucleic acid microarray" include all the devices so called in Schena (ed.), *DNA Microarrays: A Practical Approach* (*Practical Approach Series*), Oxford University Press (1999) (ISBN: 0199637768); Nature Genet. 21(1)(suppl):1-60 (1999); and Schena (ed.), *Microarray Biochip: Tools and Technology*, Eaton Publishing Company/BioTechniques Books Division (2000) (ISBN: 1881299376), the disclosures of which are incorporated herein by reference in their entireties. As so defined. the term "microarray" and phrase "nucleic acid microarray" also include substrate-bound collections of plural nucleic acids in which the plurality of nucleic acids are distributably disposed on a plurality of beads, rather than on a unitary planar substrate, as is described, inter alia, in Brenner et al., *Proc. Natl. Acad. Sci. USA* 97(4):166501670 (2000), the disclosure of which is incorporated herein by reference in its entirety; in such case, the term "microarray" and phrase "nucleic acid microarray" refer to the plurality of beads in aggregate.

In an exemplary array embodiment, the probe (or target) is immobilized on a substrate to provide an array in which each immobilized probe (or target) can be assigned a unique location (e.g. X—Y coordinate) on the substrate.

To facilitate discrimination, one or both of the probe and target can be detectably labeled.

Nucleic acid labels (and methods for their incorporation) are well known in the art, and include, inter alia, radioactive, fluorescent, and enzymatic labels. Commonly used labels include radionuclides, such as $^{32}P$, $^{33}P$, $^{35}S$, $^{3}H$ (and for NMR detection, $^{13}C$ and $^{15}N$), haptens that can be detected by specific antibody or high affinity binding partner (such as biotin), and fluorophores, such as the cyanine dyes Cy3, Cy5, phycoerythrin, and fluorescein. The probe (equally target) can be multiply labeled, or otherwise multiply derivatized, such as by incorporation of both a fluorophore and a quencher.

The hybridization reaction (or plural hybridization reactions) are performed under conditions that are suitable for association of duplexes.

Preferably the total ionic salt concentration should not exceed about 0.7 M, and should generally be less than about 100 mM, usually less than about 50 mM, more usually less than about 10 mM, with the substantial absence of salt being optimal. Without intending to be bound by theory, it is believed that the concurrent presence of 5×SSPE accounts, at least in part, for the inability of Cronin et al. U.S. Pat. No. 6,045,996, to observe increased specificity upon addition of CTAB to a microarray hybridization.

The solutions preferably have a pH ranging from pH 4 to 11, typically at least about 6, 6.5, or 7, and typically no more than about 10, typically no more than about 9, 8.5, or 8.

The specific association enhancer is present at a concentration effective to increase the rate and specificity of duplex formation.

Typically, the specific association enhancer is present at a molar ratio of at least 1:1 with respect to nucleic acid phosphates in the hybridization reaction. For cationic detergents such as CTAB, the molar ratio of cationic detergent to nucleic acid phosphate group is thus at least about 1:1, often at least 2:1, 3:1, 4:1, 5:1, 6:1, 7:1 or even at least about 8:1 or more, with integral ratios not required.

Preferably, the specific association enhancer is present at least to a concentration above which additional specific association enhancer molecules do not associate with nucleic acid phosphates in the hybridization reaction. For cationic detergents such as CTAB, the molar ratio of cationic detergent to nucleic acid phosphate group is thus at least about 8:1, and typically at least about 9:1, 10:1, 20:1, 100:1 or more, with integral ratios not required.

Expressed as a concentration, the specific association enhancer, such as cationic detergent such as CTAB, is present in a concentration of at least about 1 femtomolar, often at least about 1 nanomolar, 1 micromolar, and even at least about 1 millimolar, and can be as high as about 1 molar, typically as high as about 100 mM, often as high as about 10 mM.

For CTAB, the concentration is typically at least about 0.1 mM, often at least about 1 mM, and typically no more than about 10 mM, even no more than about 5 mM, with concentrations of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, and 2.0 mM typical, with concentration of about 1.0 mM, as exemplified below, presently preferred.

The incubation temperature is selected to provide a desired level of discrimination as among targets.

Selection of the incubation temperature will typically involve a series of routine experiments well within the skill in the art. As is well known, in such routine optimization experiments the temperature of the hybridization reaction for any given common probe and target is varied. To find a desired temperature for the methods of the present invention, the degree of duplex formation is determined as between perfectly matched and mismatched duplexes for each of the temperatures, and the temperature giving desired levels of discrimination chosen.

The temperature chosen can be that which optimizes discrimination for any given probe and target, or can be that which gives optimal discrimination as among plural targets, even though such temperature may be nonoptimal for any given one of the plural probe:target duplexes. As noted above, we have observed that the specific association enhancer reduces temperature sensitivity of duplex formation, permitting a common temperature to suffice to permit duplex formation for a variety of probe:target duplexes.

Generally, the preferred incubation temperature is below the Tm of the double-stranded nucleic acid association product. With regions of complementarity of 16-25 nucleotides, the temperature will typically be no more than about 60° C., often no more than about 59° C., 58° C., 57° C., 56° C., 55° C., 54° C., 53° C., 52° C., 51° C., 50° C., 49° C., 48° C., 47° C., 46° C., 45° C., 44° C., 43° C., or 42° C., although higher temperatures are often permissible. With regions of complementarity of 16-30 nucleotides, the temperature will typically be at least about 20° C., typically at least about 21° C., 22° C., 23° C., 24° C., 25° C., 26° C., 27° C., 28° C., 29° C., 30° C., and even at least about 31° C., 32° C., 33° C., 34° C., 35° C., 36° C., 37° C., 38° C., 39° C., 40° C., 41° C., 42° C., with temperatures of about 35-45° C., typically 42° C., often proving suitable, although lower temperatures can be permissible.

After incubation, differences in the extent of nucleic acid duplex formation between each of the nucleic acid targets and the common nucleic acid probe is determined using any standard technique that directly or indirectly reports the extent of duplex formation.

There are numerous well known methods for directly reporting the extent of duplex formation.

For example, as shown in Examples 1 and 2, below, the degree of duplex formation can be assessed by temperature-controlled, 15% PAGE, or by single base extension reactions. The degree of duplex formation can be assessed using fluorescent dyes that discriminate single-stranded from double-stranded nucleic acids, such as PicoGreen. Singer et al, *Anal. Biochem.* 249(2):228-38 (1997). RNase protection can be used to assess the degree of duplex formation for RNA:DNA duplexes, with denaturing gel analysis for evaluation. The degree of duplex formation can also be determined by differential hydroxyapatite affinity, by increased hypochromicity (UV absorbance of ds<ss DNA), or by other known techniques. As another alternative, the common probe of the methods of the present invention can be designed as a "molecular beacon", having an internal stem-and-loop that brings a covalently attached fluorophore into resonance energy transfer proximity to a quencher that is also covalently attached thereto. Binding of the probe to its target separates fluorophore and quencher, reporting the extent of duplex formation as an increase in fluorescence emission. See, e.g. Marras et al., "Multiplex detection of single-nucleotide variations using molecular beacons," *Genet. Anal.* 14(5-6):151-6 (1999).

Other, "indirect", methods for reporting the extent of duplex formation are also well known in the art. Such methods are used, for example, in current methods for genotyping single nucleotide polymorphisms (SNPs).

The target sequences that can be discriminated using the methods of the present invention can differ in sequence in as few as one nucleotide, such as by substitution, insertion, or deletion and, as noted above, can be concurrently present in highly complex nucleic acid mixtures. Accordingly, the methods of the invention described herein, and described in the exemplary embodiments of the examples below, have great significance and can be used to improve a variety of hybridization-based techniques.

For example, the methods of the present invention permit separate members of a gene family, related in sequence, to be discriminated in a complex sample of mRNA or cDNA, allowing the differential expression of such family members readily to be followed. The methods of the present invention similarly permit allelic variants of a single gene to be discriminated in a genomic sample, facilitating detection and scoring of single nucleotide polymorphisms (SNPs). The methods of the present invention improve discrimination in microarray-based analyses for measuring gene expression, analyzing genomic sequence variation, or sequencing by hybridization.

Where the specific association enhancer is a cationic detergent, such as CTAB or a CTAB-like cationic detergent, the invention further presents, in another aspect, methods to remove the specific association enhancer from the hybridization reaction, permitting the formed duplexes to be used in subsequent enzymatic steps.

As a first step, the salt concentration of the reaction mixture is increased to a level sufficient to disrupt the association of the specific association enhancer and nucleic acid duplex. Generally, increasing the ionic salt concentration to at least about 0.7 M is sufficient. The salt concentration can be increased by addition of, for example, sodium chloride.

As a second step, the specific association enhancer is removed by any of a variety of methods. For example, the enhancer can be extracted using an organic solvent (e.g. chloroform). As an alternative, the specific association enhancer can be removed using hydrophobic or cation exchange chromatography. Or, if the duplex is of suitable size, the enhancer can be removed using size exclusion chromatography. The second step can, alternatively, be simple dilution, with the diluted hybridization reaction thereafter used directly for subsequent enzymatic steps.

Furthermore, removal or dilution of the agent can be followed by one or more additional steps that facilitate subsequent reactions. For example, the hybridization reaction can, after removal or dilution of the agent, be further diluted. Where desired, the hybridization reaction can, after removal or dilution of the agent, be subjected to chromatography or dialysis or filtration.

Removal (or dilution) of association enhancer using this method allows the use of these nucleic acids in enzymatic reactions with any desired enzyme, such as those having the following enzyme activities: nuclease, polymerase, phosphatase, kinase, ligase, nucleotide transferase, methylase or other nucleic acid-specific activities.

The concomitant increase in rate and specificity of duplex formation effected by the specific hybridization enhancers described herein—further in conjunction with methods for removing cationic detergents after hybridization—can be exploited to increase the fidelity of hybridization-primed enzymatic reactions. By "hybridization-primed" is meant that the enzymatic reaction requires that there have been an antecedent hybridization, typically of at least one primer to a template.

For example, the fidelity of first strand cDNA synthesis can be improved where the mRNA template contains a plurality of similar primer binding sites. The plurality of similar primer binding sites can, e.g., arise from the concurrent presence in the mRNA template sample of transcripts of related genes, such as members of a gene family, or from the presence within a single mRNA of a plurality of sequences similar to the primer binding site. Increasing the fidelity of first strand cDNA synthesis is useful for improving subsequent synthesis of double-stranded cDNA, for improving results of 5'-RACE (rapid amplification of cDNA ends) or 3'-RACE, and for improving results in RT-PCR (reverse transcriptase polymerase chain reaction).

As another example, where a sequencing template contains a plurality of sequences similar to that at which the sequencing primer is intended to bind—either multiply present on a single template molecule, or due to contamination with other nucleic acids—addition of the specific association enhancer of the present invention to the primer annealing step will improve the specificity with which the primer binds to the desired priming site, improving sequence results.

As yet another example, a number of genetic detection approaches depend upon hybridization of a plurality of oligonucleotides to adjacent sites of a template, followed by ligation thereof. For review, see Schweitzer et al, *Curr. Opin. Biotechnol.* 12(1):21-7 (2001). Addition of the specific association enhancer of the present invention to the primer annealing step will improve the specificity with which the primers bind to the expected priming sites, improving the ability of this method to discriminate among closely related template sequences.

As yet a further example, RNase protection assays can be improved by the methods of the present invention, by increasing the rate and specificity of association of DNA:RNA hybrid duplexes, which are thereafter contacted with RNase to identify the region of protection. In one application of such improved RNase protection assays, the method is used to map regions of RNA secondary structure.

Thus, in another aspect, the invention provides a method for improving the fidelity of hybridization-primed enzymatic reactions. The method comprises hybridizing at least one probe (in this context, also denominated a "primer") to a target (in this context, also denominated a "template") in the presence of an effective amount of a specific association enhancer, wherein the at least one probe (primer) has a region of complementarity to the target (template), and then performing an enzymatic reaction on the duplexed primer.

Typically, the region of complementarity between the probe (primer) and target is at least about 15 nt in length, often at least about 16 nt, 17 nt, 18 nt, 19 nt, 20 nt, 21 nt, 22 nt, 23 nt, 24 nt, or even 25 nt, 26 nt, 27 nt, 28 nt, 29 nt, or 30 nt in length, although shorter lengths are permissible. Also typically, the region of complementarity is no more than about 30 nt in length, often no more than about 29 nt, 28 nt, 27 nt, 26 nt, 25 nt, 24 nt, 23 nt, 22 nt, 21 nt, 20 nt, 19 nt, 18 nt, 17 nt, 16 nt, or even no more than 15 nt in length, although longer lengths are permissible. Frequently, the probe (primer) is between about 16 and 30 nucleotides long, with a length of about 20 nucleotides being typical under currently tested conditions.

The region of complementarity can be present within nucleic acids that have sequence additional thereto.

Most commonly, such sequence additional to the region of complementarity is found in the template. In such embodiments, the additional portion can be of any length, with the region of complementarity positioned anywhere within the template. Indeed, the template can be 1000 nt to 100,000 nt or longer, and may encompass an entire chromosome.

Occasionally, sequence additional to the region of complementarity is found in the probe (primer). In such embodiments, the additional portion can be of any length, but is typically no more than about 200 nt, often no more than about 150 nt, 100 nt, 75 nt, 50 nt, 40 nt, 35 nt, 30 nt, 25 nt, or even no more than about 24 nt, 23 nt, 22 nt, 21 nt, 20 nt, or even no more than about 15, 16, 17, 18, or 19 nt.

As noted above, we have not observed an improvement in specificity of hybridization in DNA:DNA duplexes under the tested conditions. In typical embodiments of the methods of this aspect of the invention, therefore, the primer is DNA and the template RNA, although any combination of DNA:RNA, DNA:mDNA, RNA:RNA, and RNA:mDNA can be used, with either primer or template having the first-named of the two compositions.

The hybridization reaction is performed under conditions that are suitable for association of duplexes.

Preferably the total ionic salt concentration should not exceed about 0.7 M, and should generally be less than about 100 mM, usually less than about 50 mM, more usually less than about 10 mM, with the substantial absence of salt being optimal. The solutions preferably have a pH ranging from pH 4 to 11, typically at least about 6, 6.5. or 7, and typically no more than about 10, typically no more than about 9, 8.5, or 8.

The specific association enhancer is present at a concentration effective to increase the rate and specificity of duplex formation.

Typically, the specific association enhancer is present at a molar ratio of at least 1:1 with respect to nucleic acid phosphates in the hybridization reaction. For cationic detergents such as CTAB, the molar ratio of cationic detergent to nucleic acid phosphate group is thus at least about 1:1, often at least 2:1, 3:1, 4:1, 5:1, 6:1, 7:1 or even at least about 8:1 or more, with integral ratios not required.

Preferably, the specific association enhancer is present at least to a concentration above which additional specific association enhancer molecules do not associate with nucleic acid phosphates in the hybridization reaction. For cationic detergents such as CTAB, the molar ratio of cationic detergent to nucleic acid phosphate group is thus at least about 8:1, and typically at least about 9:1, 10:1, 20:1, 100:1 or more, with integral ratios not required.

Expressed as a concentration, the specific association enhancer, such as cationic detergent such as CTAB, is present in a concentration of at least about 1 femtomolar, often at least about 1 nanomolar, 1 micromolar, and even at least about 1 millimolar, and can be as high as about 1 molar, typically as high as about 100 mM, often as high as about 10 mM.

For CTAB, the concentration is typically at least about 0.1 mM, often at least about 1 mM, and typically no more than about 10 mM, even no more than about 5 mM, with concentrations of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, and 2.0 mM typical, with concentration of about 1.0 mM, as exemplified below, presently preferred.

The incubation temperature is selected to provide specific primer hybridization to template.

Generally, the preferred incubation temperature is below the Tm of the double-stranded nucleic acid association product. With regions of complementarity of 16-30 nucleotides, the temperature will typically be no more than about 60° C., often no more than about 59° C., 58° C., 57° C., 56° C., 55° C., 54° C., 53° C., 52° C., 51° C., 50° C., 49° C., 48° C., 47° C., 46° C., 45° C., 44° C., 43° C., or 42° C., although higher temperatures are often permissible. With regions of complementarity of 16-30 nucleotides, the temperature will typically be at least about 20° C., typically at least about 21° C., 22° C., 23° C., 24° C., 25° C., 26° C., 27° C., 28° C., 29° C., 30° C., and even at least 31° C., 32° C., 33° C., 34° C., 35° C., 36° C., 37° C., 38° C., 39° C., 40° C., 41° C., 42° C., with temperatures of about 35-45° C., typically 42° C., often proving suitable, although lower temperatures can be permissible.

The enzymatic reaction performed on the duplexed primer can be any enzymatic reaction that can be performed on duplexed, or partially duplexed, nucleic acids. The reaction can, e.g. be or include polymerization from the 3' OH group (including addition of a single nucleotide, including a single dideoxynucleotide), nuclease digestion (including 5' exonuclease digestion, 3' exonuclease digestion, and endonucleolytic cleavage, such as by restriction enzyme), phosphatasing (typically, of the 5' terminal phosphate), phosphorylation (kinasing, typically of the 3' hydroxyl), methylation, nucleotide transferase, and ligation (typically, to a primer hybridized to the template adjacent thereto).

The method is not limited to performance of a single enzymatic reaction, and can include, e.g., successive reactions on the duplexed primer or on enzymatic products of the duplexed primer.

The method can further comprise the step, after probe hybridization and before enzymatic reaction, of removing the specific association enhancer. Where the specific association enhancer is a cationic detergent, such as CTAB, the enhancer can be removed by adding salt to the hybridization reaction, followed thereafter by removal of the detergent by any of a number of methods, as described above, including extraction with an organic solvent, hydrophobic or ion exchange chromatography, or size exclusion chromatography.

As would be understood, each of the methods of the present invention above-described is, in its broadest sense, a method for increasing the specific association rate of a pair of single-stranded nucleic acid molecules, wherein the method comprises combining in a reaction mixture a first single-stranded molecule and a second single-stranded molecule in the presence of an association enhancer, the combining being under conditions suitable for specific association of the first and second molecules in a nucleic acid duplex, wherein the inclusion of the specific association enhancer in the combining step allows for formation of matched nucleic acid duplexes at an increased specific association rate. It is, therefore, a further aspect of the present invention to provide such methods.

In another aspect, the invention provides kits that facilitate performance of the methods of the present invention.

The kits of the present invention can comprise a nucleic acid suitable for use as a probe, and a container comprising an incubation solution comprising an amount of specific association enhancer suitable for accelerating specific duplex formation (particularly formation of DNA:RNA or RNA:DNA duplexes). The incubation solution can comprise other components that facilitate association at the rate and with the specificity provided by association enhancer, but is generally substantially free of components that adversely affect the ability of the association enhancer to provide the desired increased association and specificity (e.g., the incubation solution contains no salt or insignificant amounts of salt, e.g., a salt concentration that does not adversely affect activity of association enhancer in the rate or specificity of nucleic acid association). The kit can also optionally contain a detectable label for detection of nucleic acid duplexes (which detectable label can be incorporated into or be separate from the nucleic acid probe), and instructions for use.

The following examples are set forth so as to provide those of ordinary skill in the art with a complete disclosure and description of how to make and use the present invention, and are not intended to limit the scope of what the inventors regard as their invention; nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Although other methods provide for an increase in the rate of association of nucleic acid molecules, the examples set forth below demonstrate that the methods of the present invention provide the additional advantage of improved selectivity of formation of the matched nucleic acid duplex over the duplex with single nucleotide mismatch—an advantage that is surprising when viewed in light of prior methods.

The experiments for comparing association of a pair of complementary 20 nucleotide DNA oligos to pairs having one or two single nucleotide mismatches (Example 1, Table 1) show that under standard non-accelerated conditions, incubating at 42° C. (which is about 16 degrees Celsius below the Tm for the completely matched DNA:DNA duplex), the DNA:DNA duplexes with single nucleotide mismatch form equally well as those that are perfectly matched, and duplexes with two mismatches somewhat less effectively. CTAB accelerated the formation of DNA:DNA duplexes more than 300-fold, but had no observable effect on discrimination between the completely matched DNA:DNA duplex and the duplex with a single nucleotide mismatch at any position along the oligo (Example 1, Table 1). The association of DNA:DNA oligos with CTAB was performed in the presence of 50 mM NaCl. Increasing the NaCl concentration above 0.7 M totally abolished the acceleration.

Using the same complementary pair of oligos under standard, non-accelerated conditions, but with RNA and DNA, improves the selectivity of formation of matched RNA:DNA duplexes over duplexes with a single nucleotide mismatch (Example 1, Table 1). Surprisingly, addition of CTAB for acceleration of RNA:DNA duplex formation further increased discrimination against single nucleotide mismatched duplexes at all positions, as compared to standard non-accelerated conditions (Experiment 1, Table 1). Using a second, enzymatic assay for duplex detection shows that, in the presence of CTAB, the association of DNA and RNA molecule has up to 50-fold specificity (Experiment 2, Table 2).

As discussed above, a variety of methods have previously been shown to accelerate formation of nucleic acid duplex associations; to our knowledge, however, none has shown concomitant increase in specificity of association. As for prior methods of mismatch discrimination, prior methods focused in large part on exploiting the difference in Tm between matched and mismatched duplexes for discrimination of matched and mismatched species. In contrast, the present inventors have discovered that in the presence of specific association enhancers, exemplified herein by the cationic detergent CTAB, mismatched duplexes between RNA and DNA form less favorably at incubation temperatures that are significantly below their Tm, an effect not predicted by, or predictable from, prior observations or theories.

In the presence of CTAB, the specificity of association at 42° C. is optimal for 20 nucleotide-long oligonucleotides. Although specificity decreases as the length approaches 30 nucleotides—difference in Tm between the matched duplexes formed from these molecules and duplexes having a single nucleotide mismatch becoming narrower—higher specificity for longer oligos can be achieved by incubation at higher temperatures. Interestingly, oligos as short as 16 nucleotides, having Tm's about 51° C., show greatly diminished double-stranded duplex molecule formation in the reaction performed even at 37° C. This phenomenon may be attributed to the specific action of CTAB on nucleic acids that affects their ability to reassociate. As discussed above, the specificity of association of nucleic acids can be achieved by using, for example, short single-stranded nucleic acids between 8-40 nucleotides long. In practical use, oligos of 12-30 nucleotides long are often preferred.

Another consideration of relevance to the invention is determining whether varying the length of the DNA and RNA molecules, but keeping a fixed length of complementary sequence, affects the specificity of association in the presence of CTAB. The results in Table 3 (Experiment 3) show that using a longer single-stranded DNA molecule (60 nucleotides), which has only 20 nucleotides of complementary sequence, or varying the length of the RNA from 20 to 1000 nucleotides, did not affect the specificity of association. Thus, it is the length of the region of complementary sequence that is most important to the association according to the methods of the invention.

Molecules with the same length but different nucleotide compositions always displayed better selectivity in the presence of CTAB than under standard non-accelerated conditions (Example 3, Table 3). For optimal specificity, the molar concentration of complementary single-stranded molecules should be kept under 10 nM. However, the presence of heterologous single-stranded DNA or RNA in 1000 times excess over the concentration of complementary molecules affects neither efficiency nor specificity.

The acceleration of nucleic acid association in the presence of CTAB can be performed in solutions containing a total ionic concentration below 0.7 M, with the maximal specificity reached in the solutions with no salt but containing buffer. The pH of buffer can vary from about pH 4-10.

The specific association enhancers useful in the methods of the present invention appear to bind nonspecifically (that is, without sequence dependency) to nucleic acids and, when so bound, to present at least one weakly interacting, relatively unstructured, polymeric domain for intermolecular interaction With respect to the cationic detergent specific association enhancers particularly exemplified herein, it is believed (without intending to be bound by theory) that the positive charge mediates the association of the detergent with nucleic acid phosphate groups, whereas the hydrophobic side-chain acts as the polymeric domain to mediate transient, high probability, nonspecific interactions between nucleic acid molecules. One exemplary association enhancer, CTAB, falls in the class of tetraalkylammonium salts. In general the length of the alkyl chain of the tetraalkylammonium salts must be greater than about 12 carbons (Example 4, Table 4).

The counter ion of the tetraalkylammonium salts does not affect the specificity of the reaction and can be, for example, bromide, chloride, or sulfate (Example 5).

The methods of the invention can be adapted for use in solution or for use where one of the two molecules to be duplexed is immobilized on a support (e.g., a solid or semi-solid support, e.g., an array or a bead). The association between pairs of complementary nucleic acid molecules, one of which is attached to the surface and the other in solution, can display the same specificity as if both molecules were in solution.

EXAMPLE 1

Method for Using CTAB to Accelerate Rate and Increase Specificity of RNA:DNA Oligonucleotide Hybridization Detected by PAGE The standard non-accelerated hybridization was performed in solution containing 10 mM Tris-HCl (pH 8), 1 mM EDTA, 50 mM NaCl, 1 nM $^{32}$P 5'-labeled c60L20 DNA or Tch2.1L20 RNA single-stranded oligonucleotides, and 50 nM of either the complementary pm60L20 oligonucleotide or one of 20 complementary DNA oligos in which each has only a single nucleotide changed, such that every position was examined. The oligonucleotide sequences were as follows:

```
DNA         5'-                        [SEQ ID NO: 4]
c60L20:     CTGTTTCTTCTGGTGATGCT-3'

RNA         5'-                        [SEQ ID NO: 2]
Tch2.1L20:  CUGUUUCUUCUGGUGAUGCU-3'

Complemen-  5'-                        [SEQ ID NO: 1]
tary DNA    AGCATCACCAGAAGAAACAG-3'
pm60L20:

20 complementary DNA oligos each with a single nu-
cleotide change. covering all 20 positions.
```

The calculated Tm for the completely matched duplex: 58° C.

The accelerated reaction was treated the same as a non-accelerated hybridization described above, except that 0.1 nM $^{32}$P-labeled oligos and 0.1 nM complementary oligos were used, and CTAB was added to 1 mM. The mixtures were heated first at 85° C., and then incubation was continued at 42° C. for 40 min for non-accelerated, and 10 min for the CTAB-accelerated reaction. Aliquots were assayed for formation of double-stranded molecules by temperature-controlled, 15% PAGE, followed by autoradiography. The formation of double-stranded molecules was determined. Table 1 compares the efficiency of formation of completely matched duplex molecules over duplexes with a single nucleotide mismatch.

TABLE 1

Comparison of the Efficiency of Formation for Matched Duplexes and Duplexes with Single Nucleotide Mismatch detected by PAGE
Ratio: mismatched/matched

| | Duplex | | | |
|---|---|---|---|---|
| | DNA:DNA | DNA:DNA + CTAB | RNA:DNA | RNA:DNA + CTAB |
| Matched | 1[a] | 1[b] | 1[a] | 1[b] |
| Mismatched at: | | | | |
| 1 position | 1.09 | 0.91 | 1.07 | 0.86 |
| 2 position | 0.98 | 1.1 | 0.46 | 0.36 |
| 3 position | 0.85 | 1.12 | 0.46 | 0.26 |
| 4 position | 1 | 1.2 | 0.69 | 0.26 |
| 5 position | 1.09 | 0.87 | 0.45 | 0.25 |
| 6 position | 1.05 | 1.1 | 0.46 | 0.18 |
| 7 position | 1.14 | 1.14 | 0.38 | 0.21 |
| 8 position | 1.12 | 0.98 | 0.61 | 0.23 |
| 9 position | 1.03 | 1.17 | 0.30 | 0.20 |
| 10 position | 1.18 | 0.97 | 0.24 | 0.21 |
| 11 position | 1.14 | 1.11 | 0.28 | 0.16 |
| 12 position | 0.87 | 0.9 | 0.92 | 0.31 |
| 13 position | 1.07 | 1 | 0.58 | 0.28 |
| 14 position | 1.11 | 1.1 | 0.48 | 0.18 |
| 15 position | 1.18 | 0.86 | 0.7 | 0.30 |
| 16 position | 0.94 | 1.1 | 0.57 | 0.28 |
| 17 position | 0.85 | 1.18 | 0.45 | 0.27 |
| 18 position | 1.07 | 1.1 | 0.89 | 0.41 |
| 19 position | 0.94 | 0.98 | 0.97 | 0.81 |

TABLE 1-continued

Comparison of the Efficiency of Formation for Matched Duplexes and
Duplexes with Single Nucleotide Mismatch detected by PAGE
Ratio: mismatched/matched

| | Duplex | | | |
|---|---|---|---|---|
| | DNA:DNA | DNA:DNA + CTAB | RNA:DNA | RNA:DNA + CTAB |
| 20 position | 1.5 | 1.2 | 0.8 | 0.65 |
| 2 mismatches | 0.5 | 0.48 | 0.15 | 0.02 |

[a]Under the described experimental conditions 100% of the labeled DNA probe was converted to duplex product after incubation at the indicated time.
[b]Under the described experimental conditions ~50% of the labeled DNA probe was converted to duplex product after incubation at the indicated time, with no further increase following longer incubation times. Based on experiments performed under these same conditions but without CTAB, the estimated acceleration rate achieved by addition of CTAB was at least 100 times, and by extrapolation, probably over 1000 times the non-accelerated rate.

The results presented in Table 1 show that the formation of DNA:DNA duplexes, either with or without CTAB present, display no difference in the efficiency of formation of matched over mismatched DNA:DNA duplexes. In contrast, using RNA & DNA pairs some specificity can be achieved even without CTAB; however, the presence of CTAB significantly enhances this intrinsic specificity in this assay.

EXAMPLE 2

Method for Using CTAB to Accelerate Rate and Increase Specificity of Hybridization of DNA Oligonucleotide and Long RNA Molecule Assayed by Single Nucleotide Extension in an Excess of Heterologous DNA and RNA The hybridization was performed in solution containing 10 mM Tris-HCl (pH 8), 1 mM EDTA, 5 µM heterologous single-stranded DNA oligonucleotides, 0.2 mg/ml heterologous yeast total RNA, 1 mM CTAB, 0.1 nM Tch2 RNA (a single-stranded molecule about 340 nucleotides long), and 0.1 nM 32P 5'-labeled complementary pm60L20 oligonucleotide or one of a series of 20 complementary oligonucleotides having a single nucleotide changed at one position each.

The Tch2 RNA, which is about 340 nucleotides long, includes both a 279-mer sequence that is complementary to the naturally expressed mRNA and additional sequence that is appended during the T7 in vitro transcription reaction. The sequence of the 279 nt RNA sequence is as follows:

[SEQ ID NO: 5]
5'-
GAAUUCGUCCAGAUCUAUGAAUCCGUUACCGUCUAGAUCGAAUUGUUUC

AUCAUCGUUACUGUUUCUUCUGGUGAUGCUGUUGGUGAGAGAGCGCGGAU

CACUUCUUUGAGCUCGUCGACGGAGAUUUUCCCGUCGCCGUUUUUGUCGA

AUCGUUGGAAGACUUUUUUGAUGUCGUCCAUUGAUCCUAAACAGCUACGA

ACAACUCCGUUCUUCGAUGACAUUGUUGAAGAAAUUGAGAUUUUGAGAUU

UGAGAUUUGAGAGAAGAAAAAACCGAAUUC-3'

The mixtures were heated first at 85° C., and then incubation continued at 42° C. After 5 min, the reaction was stopped and the duplexes formed were assayed by single nucleotide extension. The mixture was analyzed by 15% denaturing PAGE, followed by autoradiography. Table 2 compares the efficiency of formation of completely matched duplex molecules over duplexes with a single nucleotide mismatch.

TABLE 2

Comparison of Efficiency of Formation for Matched Duplexes and
Duplexes with Single Nucleotide Mismatch Detected by Single
Nucleotide Extension
Ratio: mismatched/matched

| Matched | 1[a] |
|---|---|
| Mismatched at | |
| 1 position | 0.75 |
| 2 position | 0.27 |
| 3 position | 0.28 |
| 4 position | 0.15 |
| 5 position | 0.059 |
| 6 position | 0.034 |
| 7 position | 0.033 |
| 8 position | 0.098 |
| 9 position | 0.039 |
| 10 position | 0.094 |
| 11 position | 0.041 |
| 12 position | 0.19 |
| 13 position | 0.13 |
| 14 position | 0.15 |
| 15 position | 0.14 |
| 16 position | 0.23 |
| 17 position | 0.25 |
| 18 position | 0.31 |
| 19 position | 0.22 |
| 20 position | 0.05 |
| 2 mismatches | 0 |

[a]Under the described experimental conditions ~50% of the labeled DNA probe was converted to duplex product after incubation at the indicated time, with no further increase following longer incubation times. Based on experiments performed under these same conditions but without CTAB, the estimated acceleration rate achieved by addition of CTAB was at least 300 times, and by extrapolation, probably over 1000 times the non-accelerated rate.

The results in Table 2 show that CTAB greatly increases the specificity of formation of matched over mismatched duplexes at essentially all positions within the region of complementary sequence. Additionally, the total length of the RNA (about 340 nt) which has only a 20 nucleotide region complementary to the DNA does not decrease the specificity.

EXAMPLE 3

Use of CTAB to Accelerate Rate and Increase Specificity of Hybridization for a Number of Different DNA Oligonucleotides and RNA Molecules The hybridization was performed in solution as described in Example 2, except that different pairs of complementary DNA and RNA molecules and their mismatched counterparts were used for hybridization as follows:

1. DNA pm203.L20: 5'-ATGTCATCGAAGAACGGAGT-3' [SEQ ID NO:6] or two pm203.L20 oligonucleotides each with a single nucleotide change at either position 11 or 13 from the 5' end, and complementary to the Tch2 RNA of length about 340 nucleotides. Tm for the duplex is 58° C.
2. DNA pm60L2060: 5'-GAAATCGTCAAAATCGCTTA-CAGTTCAGGTCTCC AGTCATAGCATCACAAGAA-GAAACAG-3' [SEQ ID NO:7] or four nearly identical pm60L2060 oligonucleotides each with a single nucleotide change at positions 1, 4, 9, or 17 from the 5' end of the complementary sequence (underline) and complementary to Tch2 RNA of length about 340 nucleotides. Tm for the duplex 58° C.
3. DNA B4pm1: 5'-TGGTATGTGCTTTCTCGTGT-3' [SEQ ID NO:8] or four B4pm1 oligonucleotides each with a single nucleotide change at position 2, 4, 10, or 17, and complementary to the B4 RNA, which is about 800 nucleotides long. Tm for the duplex is 62° C.
4. DNA B4pm2: 5'-TTTAGCGGGGTGATGCCTGT-3' [SEQ ID NO:9] or four B4pm2 oligonucleotides each with a single nucleotide change at position 2, 4, 10, or 17, and complementary to the B4 RNA, which is about 800 nucleotides long. Tm for the duplex is 60° C.

TABLE 3

Comparison of the Efficiency of Formation
for different DNA:RNA pairs
Ratio: mismatched/matched

| 1. Pair of DNA:RNA | |
| --- | --- |
| Matched | 1 |
| Mismatched at: | |
| 11 position | 0.20 |
| 13 position | 0.16 |
| 2. Pair of DNA:RNA | |
| Mismatched at: | |
| 1 position | 0.98 |
| 4 position | 0.06 |
| 9 position | 0.01 |
| 17 position | 0.01 |
| 3. Pair of DNA:RNA | |
| Mismatched at: | |
| 2 position | 0.88 |
| 4 position | 0.48 |
| 10 position | 0.25 |
| 17 position | 0.052 |
| 4. Pair of DNA:RNA | |
| Mismatched at: | |
| 2 position | 0.97 |
| 4 position | 0.42 |

TABLE 3-continued

Comparison of the Efficiency of Formation
for different DNA:RNA pairs
Ratio: mismatched/matched

| 10 position | 0.09 |
| --- | --- |
| 17 position | 0.02 |

The results in Table 3 show that different probe sequences for the same or different RNA sequences retain the specificity of match over mismatch formation. Additionally, longer DNA oligos with only a 20-nucleotide long region complementary to the RNA retain this specificity.

EXAMPLE 4

The Effect of the Length of the Alkyl Chain on the Acceleration and Specificity of Hybridization The hybridization was performed in solution and using DNA oligos and RNA molecules as described in Example 2, except that the different alkylammonium bromide salts with various length alkyl chains (12, 14, 16, and 18 carbons) were added in the reaction.

| DTAB: Dodecyltrimethylammonium bromide | 12 carbons |
| --- | --- |
| TTAB: Tetradecyltrimethylammonium bromide | 14 carbons |
| CTAB: Cetyltrimethylammonium bromide | 16 carbons |
| OTAB: Octadecyltrimethylammonium bromide | 18 carbons |

TABLE 4

Comparison of Efficiency of Tetraalkylammonuim Bromide
Salts with Alkyl Chains of Various Length

| 1. DTAB | |
| --- | --- |
| Matched | 0 |
| Mismatched at: | |
| 2 position | 0 |
| 4 position | 0 |
| 10 position | 0 |
| 17 position | 0 |
| 2. TTAB | |
| Matched | 1 (0.5 compared to CTAB) |
| Mismatched at: | |
| 2 position | 0.17 |
| 4 position | 0.187 |
| 10 position | 0.045 |
| 17 position | 0.09 |
| 3. CTAB | |
| Matched | 1 |
| Mismatched at: | |
| 2 position | 0.096 |
| 4 position | 0.15 |
| 10 position | 0.016 |
| 17 position | 0.076 |
| 4. OTAB | |
| Matched | 1 (1.0 compared to CTAB) |
| Mismatched at: | |
| 2 position | 0.16 |
| 4 position | 0.19 |

TABLE 4-continued

Comparison of Efficiency of Tetraalkylammonuim Bromide Salts with Alkyl Chains of Various Length

| | |
|---|---|
| 10 position | 0.022 |
| 17 position | 0.099 |

The results from Table 4 show that decreasing the alkyl chain length to 12 carbons abolishes the acceleration of DNA: RNA hybrid formation. The rest of the compounds, which have an alkyl chain longer than 12 carbons, display equal specificity and similar efficiency of DNA:RNA hybrid formation as with CTAB itself.

EXAMPLE 5

Counter-Ion of Tetraalkylammonium Salt has no Effect on Specificity of Hybridization The hybridization was performed in solution and using DNA oligos and RNA molecules as described in Example 2, except that different alkylammonium salts with various counter-ions were added in the reaction.

CTAB: Cetyltrimethylammonium bromide
CTAC: Cetyltrimethylammonium chloride
CTAS: Cetyltrimethylammonium hydrosulfate

TABLE 5

Comparison of Efficiency of Tetraalkylammonuim Salts with Various Counter-ions

| | |
|---|---|
| 1. CTAB | |
| Matched | 1 |
| Mismatched at: | |
| 2 position | 0.11 |
| 4 position | 0.186 |
| 10 position | 0.022 |
| 17 position | 0.081 |
| 2. CTAC | |
| Matched | 1 (0.7 compared to CTAB) |
| Mismatched at: | |
| 2 position | 0.11 |
| 4 position | 0.087 |
| 10 position | 0.01 |
| 17 position | 0.05 |
| 3. CTAS | |
| Matched | 1 (0.8 compared to CTAB) |
| Mismatched at: | |
| 2 position | 0.08 |
| 4 position | 0.125 |
| 10 position | 0.01 |
| 17 position | 0.1 |

The results from Table 5 show that the counter-ion has no significant effect on the efficiency or specificity of DNA:RNA hybrid formation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of performing a hybridization-primed enzymatic reaction, comprising:
    hybridizing at least one nucleic acid primer to a nucleic acid template in the presence of a specific association enhancer in a reaction mixture, wherein said at least one primer has a region of complementarity to said template, said hybridizing providing for nucleic acid duplexes, and then
    adding salt to the reaction mixture to provide a salt concentration in the reaction mixture sufficient to disrupt association of the specific association enhancer and the nucleic acid duplex;
    removing the specific association enhancer from the reaction mixture; and
    performing an enzymatic reaction on said nucleic acid duplex.

2. The method of claim 1, wherein said primer is DNA and said template is RNA.

3. The method of claim 1, wherein said primer is RNA and said template is DNA.

4. The method of claim 1, wherein said specific association enhancer is a cationic detergent.

5. The method of claim 4, wherein said cationic detergent is tetradecyltrimethylammonium salts, cetyltrimethylammonium salts, or octadecyltrimethylammonium salts.

6. The method of claim 5, wherein said cationic detergent is cetyltrimethylammonium bromide (CTAB), cetyltrimethylammonium chloride(CTAC), cetyltrimethylammonium hydrosulfate (CTAS), tetradecyltrimethylammonium bromide (TTAB), or octadecyltrimethylammonium bromide (OTAB).

7. The method of claim 6, wherein said cationic detergent is cetyltrimethylammonium bromide.

8. The method of claim 1, wherein said enzymatic reaction is polymerization, nuclease digestion, phosphatasing, phosphorylation, methylation, or ligation.

9. The method of claim 8, wherein said enzymatic reaction is polymerization.

10. The method of claim 1, wherein said removing is by extraction with an organic solvent.

11. The method of claim 1, wherein said removing is by chromatography.

12. The method of claim 11, wherein chromatography is hydrophobic chromatography, cation exchange chromatography, or exclusion chromatography.

13. A method of preparing a nucleic acid duplex formed in a hybridization-primed reaction for use in an enzymatic reaction, comprising:
    hybridizing at least one nucleic acid primer to a nucleic acid template in the presence of a specific association enhancer in a reaction mixture, wherein said at least one primer has a region of complementarity to said template, said hybridizing providing for nucleic acid duplexes, and then
    adding salt to the reaction mixture to provide a salt concentration in the reaction mixture sufficient to disrupt association of the specific association enhancer and the nucleic acid duplex; and
    removing the specific association enhancer from the reaction mixture;
    wherein a nucleic acid duplex suitable for use in an enzymatic reaction is produced.

14. The method of claim 13, wherein said removing is by extraction with an organic solvent.

15. The method of claim 13, wherein said removing is by chromatography.

16. The method of claim 15, wherein chromatography is hydrophobic chromatography, cation exchange chromatography, or exclusion chromatography.

17. The method of claim 13, wherein said primer is DNA and said template is RNA.

18. The method of claim 13, wherein said primer is RNA and said template is DNA.

19. The method of claim 13, wherein said specific association enhancer is a cationic detergent.

20. The method of claim 19, wherein said cationic detergent is tetradecyltrimethylammonium salts, cetyltrimethylammonium salts, or octadecyltrimethylammonium salts.

21. The method of claim 19, wherein said cationic detergent is cetyltrimethylammonium bromide (CTAB), cetyltrimethylammonium chloride (CTAC), cetyltrimethylammonium hydrosulfate (CTAS), tetradecyltrimethylammonium bromide (TTAB), or octadecyltrimethylammonium bromide (OTAB).

22. The method of claim 19, wherein said cationic detergent is cetyltrimethylammonium bromide.

23. The method of claim 13, wherein the specific association enhancer is a cationic detergent and in said adding step, the salt concentration of the reaction mixture is increased to greater than 0.7 M total ionic salt concentration.

24. The method of claim 23, wherein said enzymatic reaction is selected from the group consisting of: polymerization, nuclease digestion, phosphatasing, phosphorylation, methylation, and ligation.

25. The method of claim 23, wherein said enzymatic reaction is polymerization.

26. The method of claim 13, further comprising
    after said removing, performing an enzymatic reaction on the nucleic acid duplex.

* * * * *

UNITED STATES PATENT AND TRADEMARK OFFICE
CERTIFICATE OF CORRECTION

PATENT NO. : 7,482,125 B2 Page 1 of 1
APPLICATION NO. : 11/590281
DATED : January 27, 2009
INVENTOR(S) : Eugeni Namsaraev It is certified that error appears in the above-identified patent and that said Letters Patent is hereby corrected as shown below:

Column 1, Lines 15-20:

- Please replace lines 15-20 with:

"FEDERALLY-SPONSORED RESEARCH
    OR DEVELOPMENT

This invention was made with Government support under contract HG000205 awarded by the National Institutes of Health. The Government has certain rights in this invention."

Signed and Sealed this

Twenty-sixth Day of May, 2009

JOHN DOLL
*Acting Director of the United States Patent and Trademark Office*